United States Patent
Baratta

Patent Number: 5,740,809
Date of Patent: *Apr. 21, 1998

[54] NONINVASIVE INFRARED BLOOD FLOW DETECTOR

[76] Inventor: Francis I. Baratta, 138 Ridge St., Arlington, Mass. 02174-1737

[*] Notice: The terminal 10 months of this patent has been disclaimed.

[21] Appl. No.: 329,299

[22] Filed: Oct. 26, 1994

[51] Int. Cl.$^6$ .................................. A61B 6/00
[52] U.S. Cl. .......................... 128/664; 128/745; 374/130
[58] Field of Search ........................... 128/736, 664, 128/653.1, 745, 633; 374/130

[56] References Cited

U.S. PATENT DOCUMENTS

| | | | |
|---|---|---|---|
| 4,393,366 | 7/1983 | Hill | 382/6 |
| 4,626,686 | 12/1986 | Pompei et al. | 250/342 |
| 4,797,840 | 1/1989 | Fraden | 128/736 |
| 4,849,885 | 7/1989 | Stillwagon et al. | 128/736 |
| 4,854,730 | 8/1989 | Fraden | 128/736 |
| 5,025,785 | 6/1991 | Weiss | 128/633 |
| 5,115,815 | 5/1992 | Hansen | 128/736 |
| 5,143,080 | 9/1992 | York | 128/736 |
| 5,199,436 | 4/1993 | Pompei et al. | 128/664 |
| 5,318,029 | 6/1994 | Palese | 128/736 |

*Primary Examiner*—Marvin M. Lateef
*Assistant Examiner*—Eleni Mantis Mercader
*Attorney, Agent, or Firm*—Jeffrey D. Marshall

[57] ABSTRACT

This invention detects blood flow disorders by comparing the core body temperature, defined by a tympanic membrane measurement, to temperature measurements at various locations within the eye. The differential between the temperature measurement of the core body and that of selected site locations can yield an accurate indication of blood flow disorder within the eye. Areas at the back of the eye can be scanned at selected sites to obtain a temperature measurement profile, and again these temperatures will provide a difference when compared to the core body temperature and that can indicate abnormal blood flow. The use of additional instrumentation via computer technology or photography can be employed to map the fundus area of the eye and produce hard copies of results. The same principle can be utilized to determine abnormal blood flow patterns at subsurface skin locations caused by infections, disease, peripheral circulation, soft tissue intimation due to sprains, arthritis tendinitis, etc., vasodilation, and exposure to external environment.

10 Claims, 3 Drawing Sheets

NONINVASIVE INFRARED BLOOD FLOW DETECTOR

RELATED U.S. APPLICATION DATA

Disclosure Document No. 357218, July 1994
Patent application Ser. No. 08/199,636
REFERENCES CITED
U.S. Patent Documents
U.S. Pat. No. 4,626,686, December 1986, Pompei, et al.
U.S. Pat. No. 4,797,840, January 1989, Fraden
U.S. Pat. No. 5,199,436, April 1993, Pompei, et al.
OTHER PUBLICATIONS
"Inter-Individual Variation in Blood Supply of the Optic Nerve Head", S. S. Hayreh, Documenta Ophthalmologica, Vol. 59, 217–246, 1985.
"Body Surface Temperature", J. M. Looney, Jr., Measurements and Control, 1989.
*Gray's Anatomy, 35th British Edition,* eds. R. Warwick and P. L. Williams, W,B. Saunders Co., Philadelphia, 1973.
"Choroidal Blood Flow as a Heat Dissipation Mechanism in the Macula", L. M. Parver, C. Auker, and D. O. Carpenter, American Journal of Ophthalmology, Vol. 89, 641–646, 1980.
"Ear Thermometry", J. M. Looney, Jr., and F. Pompei, Medical Electronics, 1989.

FIELD OF INVENTION

This invention relates to the detection of temperature in the human body, such as in the back of the eye or on the surface of the body and compares it to the core body temperature. The differential between these temperatures and the previously measured core body temperature, defined by a tympanic membrane measurement, yields an accurate absolute measure of the temperature of the blood at selected locations. The temperature differences can be related to blood flow disorder in the human eye that can be an indication of disease. If the measurements are taken on the surface of the body, the differences can also be related to medical problems.

SUMMARY OF INVENTION

The eyes provide a direct view of a portion of the circulatory system when several sites on the choroidal area are examined. Changes that take place in abnormal blood flow circulation in the back of the eye can help in diagnosis of certain diseases and possibly their cure if detected soon enough. These diseases and others also affect sight in both the long and short-term. There are five diseases of the eye that are generally termed vascular retinopathies which result from interference with the blood supply to the eyes, these are: central retinal artery occlusion, central retinal vein occlusion, diabetic retinopathy, hypertensive retinopathy, and sickle cell retinopathy. In addition, there are other blood flow related diseases such as: retinal infection, retinal hemorrhaging including tumors and cysts, arteriosclerosis, and macula degeneration related to abnormal choroidal circulation. Such maladies can lead to serious sight problems and eventually cause blindness.

The presently proposed invention incorporates an infrared detector that measures the difference between the temperature of the tympanic membrane, which represents the core body temperature as a base reference, and the temperature of the choroidal tissue of the eye. A temperature difference can be blood flow related and if greater than a predetermined threshold value can indicate a blood flow disorder. Thus, this device and technique can be used as a diagnostic tool by ophthalmologists to scan the flow of blood in the choroid and determine if disorders exist.

Note also, that the same device can be adapted as a diagnostic tool to scan and measure the surface temperature of the human body to indicate medical problem areas in a subject.

BACKGROUND OF THE INVENTION AND PRIOR ART

Background:

The choroid carries the main vascular supply to the back of the eye. Many diseases of the eye are blood flow related, which can be caused by an abnormal blood supply from the choroid, see "Inter-Individual Variation in Blood Supply of the Optic Nerve Head", by S. S. Hayreh, Documenta Ophthalmologica Vol. 59, P 217–246, 1985. For example, vascular retinopathies are noninflammatory retinal disorders that result from interference with the blood supply to the eyes. The five distinct types of vascular retinopathy are central retinal artery occlusion, central retinal vein occlusion, diabetic retinopathy, hypertensive retinopathy, and sickle cell retinopathy. There are additional eye disorders which are: macular degeneration, caused by abnormal blood vessels in the macula or arteriosclerosis of the arteries in the retina; optic atrophy, which can be caused by central retinal artery or vein occlusion, optic neuritis, which is inflammation of the optic nerve; retinatblastoma, a malignant tumor of the retina that affects infants and babies.

Also, cutaneous blood flow patterns may be indications of infection, disease, peripheral circulation (thrombophlebitis, arterial vasculitis, etc.), soft tissue inflammation due to sprains, arthritis, tendinitis, etc., vasodilation as a result of regional block or a drug regimen, and exposure to external environment.

Temperature Detection:

Temperature measurement is important because it is highly variable between individuals and is dependent on other medical factors (i.e., it is above "normal" if the body is fighting infection). The basic problem of current detection devices is that they measure their own temperature; not the temperature of the subject, and that they develop an absolute number which does not allow for variations in individuals.

Acceptable clinical methods measure core body temperature under the tongue or in the rectum, and consist of utilizing a thermal probe, such as a mercury thermometer, or an electronic display device using a thermocouple or a thermistor. The basic problem not met by all three of these devices is that they measure their own temperature; not the temperature of the subject. Utilization of these instruments requires intimate contact for a sufficient length of time to raise their temperature to nearly that of the patient. Also, when attempting to determine sublingual temperature these devices will yield inaccurate readings by at least several degrees, if they are not properly located under the tongue. Further, if these instruments are not left in place long enough to equilibrate; incorrect readings will result. The behavior of the subject will also affect the accuracy of these devices, such as: breathing, speaking, movement of the probe from under the tongue, smoking and consumption of hot or cold liquids.

The surface temperature of the human body cannot be defined by any single normal value. It will change at a rapid rate in response to its external environment or its internal control mechanism, see for example "Body Surface Temperature", by J. M. Looney, Jr., Measurements and Control, 1989. A temperature value is so variable over the body surface that it raises question as to its significance and yet it is a remarkable indication of the underlying body physiology. However, using infrared techniques, accurate surface temperature changes are easily detected and can be precisely delineated. Internal body core temperature changes can be easily and quickly detected by using infrared techniques via the tympanic membrane.

Blood flow disorder detection in the eye:

Diagnostic techniques for many of the eye disorders described above, usually entail visual acuity and ophthalmoscopic examinations. For example, examination for macular degeneration to evaluate the blood pattern in the eye and detect the presence of abnormal blood vessels requires the use of fluorescein angiography. This latter technique utilizes an invasive injection of a chemical dye and photography to record blood flow patterns. Also, the routinely used fundus camera is not capable of taking angiograms fast enough to be effective in normal eyes because the choroidal vascular bed fills to rapidly with fresh blood.

Surface and subsurface blood flow disorder detection:

Most of the published clinical data on body surface temperature measurements are based on the use of infrared thermography. Infrared thermography shows the surface temperature profile in color or shades of gray. The clinical information is shown in relative temperature profiles. The technique is effective but the equipment is expensive and requires a trained operator.

DESCRIPTION OF THE INVENTION

It is seen from the above discussion that there is a need for a convenient low cost noninvasive blood flow detector that is easy to employ, yet be accurate and effective without causing a traumatic experience while being used on infants and adults, including elderly patients.

If blood flow is restricted or increased above normal in the choroid and blood vessels in the eye, local temperatures will decrease or increase, accordingly. Very accurate temperatures can be measured by infrared thermometry (IR). The present day IR sensors with their electronic instrumentation, which are used to measure core body temperature via the tympanic membrane, are accurate to within 0.10 C over a wide range of temperatures and have a response time of less than a second, see "Ear Thermometry", by J. M. Looney, JR., and F. Pompei, Medical Electronics, 1989, and U.S. Pat. No. 5,199,436.

An IR detector can be focused, either with or without the aid of the lens of the eye, on an emerging beam from the back of the eye where the choroid and internal blood vessels are located. Temperature within the eye can be referenced to the body core temperature via use of a tympanic measurement incorporated in the device. In this way accurate differential temperature readings encompassing a small area not previously available can be established to determine the lack of or increase in blood flow. The use of present day-state-of the art instrumentation to scan the eye and map the fundus area can be utilized. Computer technology can be employed and produce hard copies of the results.

It is well known by ophthalmic researchers that if a pressure surge is applied to the eye by means of a vacuum cup, or other devices, the intra-ocular pressure is momentarily disrupted and the eye will compensate for the increase in pressure such that in a relatively short time the pressure returns to its original level. The rate of recovery in each individual will differ, which may be an indication of the state of health of the subject's eyes. By accurately tracking this phenomenon as a function of time, it could prove to be a valuable diagnostic indicator. This can be accomplished by the proposed invention by measuring the change in temperature as a function of time to determine the recovery rate of a patient's eyes after an imposition of applied pressure. Also, by calibrating the temperature at the macula and fovea sites to pressure (see application Ser. No. 08/199,636, entitled "Noncontacting Portable Infrared Intra-ocular Pressure Sensor"), the potential susceptibility of the patient to impending glaucoma may be realized.

This invention presents an improved way to determine directly the temperature of various locations within the human eye through the use of a noncontacting, nonirritating, infrared temperature sensing device. This is accomplished by accurately measuring the core body temperature as the individual's base temperature and the temperature at various sites located at the choroid of the eye using the same tympanic temperature measuring device. The difference in these temperatures can reveal the potential danger of blood flow disorders. A visual read-out can easily be incorporated in the device. The same device can be adapted as a diagnostic tool to scan and measure the surface temperature of the human body to indicate medical problem areas in a subject. The device can be employed as an accurate temperature sensing instrument for diagnostic purposes.

Tympanic temperature measurements are readily obtained from the present state-of-the-art commercially available devices. They utilize the output of a thermopile and support electronics that respond to sensed radiation. The housing of such devices incorporates a disposable conical speculum that is inserted into the ear canal for measurement of the tympanic temperature. An eye piece for stand-off can be incorporated to hold a Fresnel lens, as described in U.S. Pat. No. 4,626,686, and also mentioned in U.S. Pat. No. 4,797, 840, to reduce the field of view received by the IR detector in the tympanic measurement instrument so that the emerging beam diameter, which is near parallel, is less than than that of the pupil of the eye. The emerging IR beam can easily detect the temperature of an area as small as 50 microns within the eye. Note that pupil diameters can range from 1 mm to 8 mm in size. See *Gray's Anatomy, 35th British Edition*, eds. R. Warwick and P. L. Williams, W.B. Saunders Co., Philadelphia, 1973. According to the former patent such a device can be matched to the lens of the IR sensor so as to provide the same original flux density independent of the field of view.

The eye piece can be made of the same material as the disposable speculum used in practice, e.g., a polyethylene polymer, but of a dark hue so that the pupil of the eye will not contract. Alternatively, the pupils can be dilated if required. Note that the other eye should be closed or covered and preferably the test conducted in subdued light such that the pupils of both eyes will not contract. This will allow the full field of view of the IR beam to be transmitted from the back of the eye through the lens system and pupil of the eye to the detector. However, care must be taken so that the eyes are not exposed to bright background light, else the light-generated thermal load or the photochemical process produced by the focussing of the eye's optical system may cause an increase in temperature, see "Choroidal Blood Flow as a Heat dissipation Mechanism in the Macula", Parver et al., American Journal of Ophthalmology, Vol. 89, 1980. Barring such an occurrence, the temperature differences measured at chosen sites on the choroid within the eye referenced to arterial or venous locations by the Noninvasive Infrared Blood Flow detector, will reveal abnormal temperature sites. Such sites can be mapped by a present day state-of-the art computer oriented tracking system, which can input angles, focal information, and referent arterial locations into a visible or storable plot.

BRIEF DESCRIPTION OF DRAWINGS

The foregoing and other objects, features and advantages of the invention will be apparent from the following more particular description of preferred embodiments of the invention, as illustrated in the accompanying drawings. The drawings are not necessarily to scale, emphasis instead being placed upon illustrating the principles of the invention.

PREFERRED EMBODIMENT

An infrared device, such as that described in U.S. Pat. No. 5,199,436, is first employed to obtain a body core temperature signal by inserting in the ear canal a tympanic temperature detector and then focusing it on to the choroid at the back of the eye to obtain temperature signals from selected spot locations. The electronic signals are programmed by the device to provide a temperature difference display at selected sites of blood flow in terms of temperature. Such sites can be mapped by a present day state-of-the art computer oriented tracking system, which can input angles, focal information, and referent arterial locations into a visible or storable plot. Since this technology is available it is not further described.

Application of a pressure surge to the eye via a vacuum cup and the ensuing pressure-time curve can also be determined and recorded using this device with the addition of appropriate electronic circuitry. However, since such circuitry is well within the state-of-the art and not pertinent to the understanding of the basic principle, it also is not discussed further.

However, a subsequent discussion provides the electronic circuitry and the mathematical process which are basic to the blood flow disorder detector is presented in the paragraphs that follow.

Figure 1:
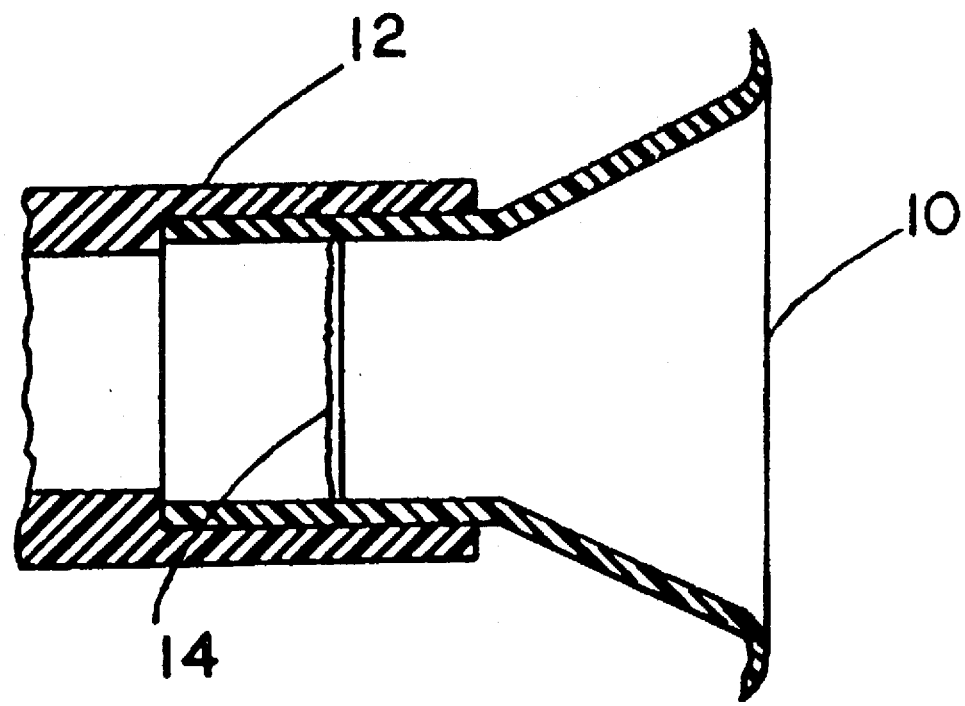
FIG. 1 is a cross-sectional view of the eye piece and Fresnel lens assembly.

FIG. 1 shows the eye piece assembly 10 held in the distal end of the tympanic temperature detector 12 by a light interference fit, and the fresnel lens 14 within the barrel of the eye piece assembly. The eye piece assembly is used as a stand-off so that the instrument would not inadvertently be poked in the eye. A Fresnel lens 14 is employed to reduce the field of view of the IR detector in the tympanic temperature measurement instrument so that the emerging beam diameter is less than that of the pupil of the eye. (Note that an IR beam can be focussed as small as 50 microns.) Yet, the assembly is designed to still provide the original flux density independent of the field of view, see U.S. Pat. No. 4,626,686.

When the tympanic temperature detector is inserted in the ear canal a disposable conical speculum is placed over the distal end of the unit for sanitary reasons. Since this a standard design for such devices, it is neither shown nor discussed here. However, again referring to FIG. 1, which shows the eye piece assembly 10, a disposable conical speculum can easily be adapted to be the same outside diameter of this assembly, such that it also fits snugly into the bore of the temperature detector 12.

The temperature sensing device can readily be designed so as to be portable or attached on a track which is mounted on 'the unit', as it is commonly called, which is standard ophthalmology equipment. This unit, an articulated frame housing various ophthalmoscopic instruments is used to locate and focus said instruments into the patient's eyes by the ophthalmologist. The temperature sensing device, mounted to the unit, such that, as previously described, is first located and inserted within the patient's ear to measure the tympanic temperature and then the unit is rotated approximately 90 degrees and focused into the eye to measure temperatures at other selected sites.

Figure 2:
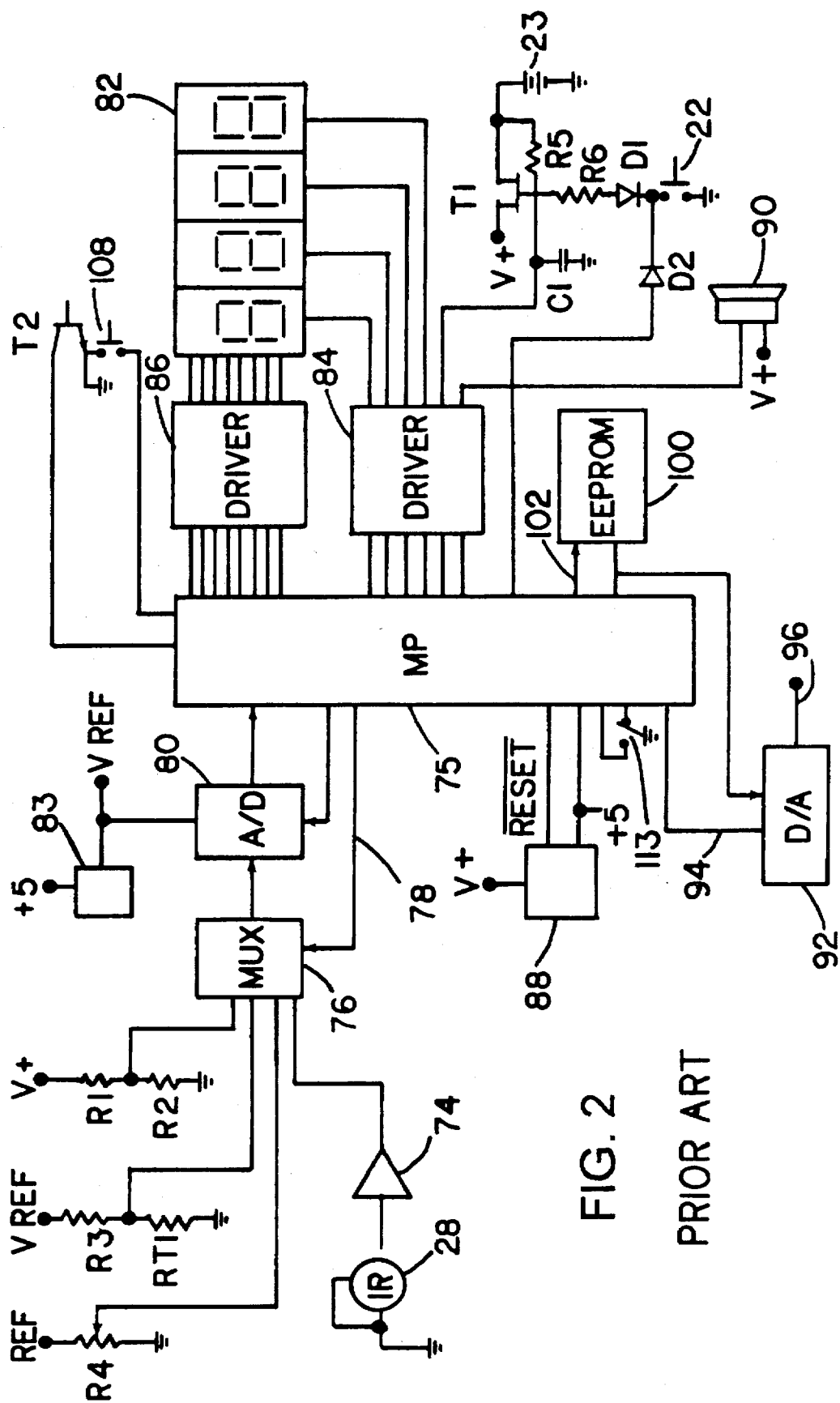
FIG. 2 is a block diagram of the electronic circuit of the detector.

A schematic of the electronics is illustration in FIG. 2 of the infrared temperature detector. The circuitry is the same as that of U.S. Pat. No. 5,199,436, except the microprocessor is programmed such that sequence of events are different than that of the referred patent. This will subsequently be described. The detector provides a readout on display 82 in response to the signal from the thermopile 28. The system is based on a microprocessor 75, which processes software routines included in read only memory within the processor chip. The processor may be a 6805 processor sold by Motorola or any variety of others. The voltage generated across the thermopile 28 due to a temperature differential between the hot and cold junctions is amplified in an operational amplifier 74. The analog output from the amplifier 74 is applied as one input to the multiplexer 76. Another input to the multiplexer 76 is a voltage taken from a voltage divider R1, R2 which is indicative of the potential V+ from the power supply 23. A third input to the multiplexer 76 is the potential across the thermistor RT1 mounted in the bore of the unit (refer to FIG. 2 of U.S. Pat. No. 5,199,436). The thermistor RT1 is coupled in a voltage divider circuit with R3 across a reference potential VRef. The final input to the multiplexer is a potential taken from the potentiometer R4, which may be adjusted by the user. The system may be programmed to respond to that input in many ways. In particular, the potentiometer may be used as a gain control or as a DC offset control. At any time during the software routine of the microprocessor 75, one of the four inputs may be selected by the select lines 78. The selected analog signal is applied to a multiple slope analog system 80, used by the microprocessor in an integral analog-to-digital conversion 80. The subsystem 80 may be a TSC500A sold by Teledyne. It utilizes the reference voltage VRef from from a reference source 83. The microprocessor 75 responds to the output from the convertor 80 to generate a count indicative of the analog input to the convertor. The microprocessor drives four 7-segmented LED displays 82 in a multiplexed fashion. Individual displays are selected sequentially through a column driver 84, and within each selected display the seven segments are controlled through segment driver 86.

When switch 22 is pressed by the user, it closes the circuit from the battery 23 through the resistors R5 and R6; and diode D1 to ground. The capacitor C1 is quickly charged and the field effect transistor T1 is turned on. Through transistor TI and the V+ potential from the storage cell 23 is applied to a voltage regulator 88, which provides the regulated +5 volts to the system. It also provides a reset signal to the microprocessor. The reset signal is low until the +5 volt reference is available and thus holds the microprocessor in a reset state. When the +5 volts is available, the reset signal goes high, and the microprocessor begins its programmed routine.

When the switch 22 is released, it opens its circuit, but a charge is maintained on capacitor C1 to keep transistor T1 on. Thus, the system continues to operate. However, the capacitor C1 and transistor T1 provide a very simple watchdog circuit. Periodically, the microprocessor applies a signal through driver 84 to the capacitor C1 to recharge the capacitor and thus keep the transistor T1 on. If the microprocessor should fail to continue in its programmed routine, it fails to charge the capacitor C1 within a predetermined time during which the charge on C1 leaks to a level at which transistor T1 turns off. Thus, the microprocessor must continue on its programmed routine or the system shuts down. This prevents spurious readings when the processor is not operating properly. With transistor T1 on, the switch 22 can be used as an input through diode D2 to the microprocessor to initiate any programmed action of the processor.

In addition to the display, the system has a sound output 90, which is driven through the driver 84 by the microprocessor.

In order to provide an analog output from the detector, a digital-to-analog convertor 92 is provided. When selected by the microprocessor through line 94, the digital convertor converts serial data to an analog output through line 96 made available to the user.

Both calibration and characterization data required for processing by the microprocessor may be stored in the electrically erasable programmable read only memory (EEPROM) 100. The EEPROM may, for example, be a 93c46 sold by CMOS Technologies, Inc. The data may be stored in the EEPROM by the microprocessor when the EEPROM is selected by line 102. Once stored in the EEPROM, the data is retained even after power down. Thus, though electrically programmable, once programmed the EEPROM serves as a virtually nonvolatile memory.

Prior to shipment, the EEPROM may be programmed through the microprocessor to store calibration data for calibrating the thermistor and thermopile. Further, characterization data which defines the personality of the of the infrared detector may be stored. For example, the same electronics hardware, including the microprocessor 75 with its internal program, may be used to determine temperature at the tympanic membrane or at various locations within the eye. The output of the device is accurate in the target temperature of about 60 degrees F. to 110 degrees F. Further, different modes of operation may be programmed into the system. For example several different uses of the sound source 90 are available.

Absolute differences can be attained by proper calibration of the detector which can be readily determined, and the EEPROM can be easily programmed by means of an optical communication link which includes a transistor T2 associated with the display 82. A communication boot may be placed over the read-out end of the detector during the calibration/characterization procedure. A photodiode in the boot generates a digitally encoded optical signal which is filtered and applied to the detector T2 to provide an input to the microprocessor 75. In a reverse direction, the microprocessor may communicate optically to a detector in the boot by flashing specific segments of the digital display 82. Through that communication link, an outside computer can monitor the outputs from the thermistor and the thermopile and perform a calibration of the devices. A unit to be calibrated is pointed at each of two black body radiation sources while the microprocessor 75 converts the signals and sends the values to the external computer. The computer is provided with the actual black body temperatures and ambient temperature in the controlled environment of the detector, and computes calibration variables and returns those variables to be stored in the EEPROM. Similarly, data which characterizes a particular radiation detector may be communicated to the microprocessor for storage in the EEPROM.

A switch 113 may be provided either internally or through the housing to the user to set a mode of operation of the detector. By positioning the switch at either the lock position, the scan position, or a neutral position; any three of the modes may be selected. The first mode is the normal scan mode where the display is updated continuously. A second mode is a lock mode where the display locks after a selectable delay and then remains frozen until the power is cycled or, optionally, the power-on button is pushed. The sound source may be caused to sound at the time of the lock. The third mode is the peak mode where the display reads the maximum value found since power-on is initiated until power is cycled or, optionally, the power-on button is pushed.

The processor determines when the voltage from the divider R1, R2 drops below each of the two thresholds. Below the higher threshold, the processor periodically enables the sound source to indicate that the battery is low and should be replaced, but allows continuous readings from the display. Below the lower threshold, the processor determines that any output would be unreliable and no longer displays temperature readings. The unit would then shut down upon release of the power button.

The present system utilizes the same state-of-the-art computations as that of U.S. Pat. No. 5,199,436, regarding: the target temperature ($T_r$, the gain calibration factor ($K_h$), the hot junction temperature ($V_j$), the Seebeck coefficient (Atav), and the actual sensor output ($V_s$). Because these formulae are fully discussed in the above named patent they are not presented or discussed here.

To determine the temperature, the microprocessor makes several computations: First the signal from the thermistor RT1 is converted to temperature using a linear approximation.

The temperature is represented by a set of linear equations, such as $$T = M(x - x_o) + b \qquad (1)$$

where M is the slope of a straight line approximation, x is an input and $x_o$ is an input end point. The values of M, $x_o$ and b are stored in the EEPROM after calibration. Thus, to obtain temperature from the thermistor, the microprocessor determines from the values of $x_o$, the line segment in which the temperature falls and then performs the computation for T based on the variables M and b stored in the EEPROM.

Secondly, the hot junction temperature is computed. A fourth power representation of the hot junction temperature is then obtained by a look up table in the processor ROM.

Thirdly, the sensed radiation may be corrected using the gain calibration factor $K_h$, the sensor gain temperature coefficient $T_{co}$, the average of the hot and cold junction temperatures and a calibration temperature $T_z$ is stored in the EEPROM. The corrected radiation signal and the fourth power of the hot junction temperature are summed and the fourth root is taken. The fourth root calculation is also based on a linear approximation which is selected according to the temperature range of interest for a particular unit. Again, the break points and coefficients for each linear approximation are stored in the EEPROM and are selected as required.

As in U.S. Pat. No. 5,199,436, there is an additional factor based on ambient temperature which also has to be included as an adjustment. The temperature of the ear $T_e$ and that of the eye $T_i$, which are sensed by the thermopile, are neither the core temperature nor the eye temperature. There is a thermal resistance between the core temperature $T_{cr}$ and $T_e$, as well as a thermal resistance between the temperature $T_v$, at the selected site(s) of the choroid and the eye temperature $T_i$. Further, there is a thermal resistance between the sensed ear temperature and ambient temperature, and similarly there is a thermal resistance between the sensed eye temperature and ambient temperature. Thus the sense temperature $T_e$ is a function of the core temperature and ambient temperature. Accordingly, the sense temperature $T_i$ is a function of the choroid temperature and the ambient temperature. Therefore, these temperatures, $T_{cr}$ and $T_v$, are shown calculated in the paragraphs that follow.

The core temperature can be computed as $$T_{cr}=T_a+(T_e-T_a)/K_{ce} \qquad (2)$$

The above is based on an assumed constant $K_{ce}$, which is a measure of the thermal resistance between $T_{cr}$, $T_e$ and $T_a$.

Similarly, the temperature at the choroid can be computed as $$T_v=T_a+(T_i-T_a)/K_{ci} \qquad (3)$$

And as before, the above is based on an assumed constant Kci, which is a measure of the thermal resistance between Ti and Ta.

These computations can account for a difference of from one-half to one degree between the objectively desired temperatures and the sensed temperatures, depending on ambient temperature.

A similar computation can be made in other applications. For example, in difference cutaneous temperature scanning, the significance of a given differential reading may be ambient temperature dependent.

The difference between core temperature $T_{cr}$ and the temperature of the choroid $T_v$, at selected locations can represent a blood flow disorder. This difference, delta $T_{bf}$ is described by equation 4:

$$\text{delta } T_{bf}=T_{cr}-T_v \qquad (4)$$

The microprocessor may be readily programmed for delta $T_{bf}$ determination such that when the unit is placed in the ear canal and switch 23 is first pressed, the temperature $T_e$ will be sensed and $T_{cr}$ will be determined according to equations 1 and 2; then the microprocessor will store and hold that data. While the unit is aimed at the eye, as previously described, and switch 23 is activated the second time, the temperature $T_i$ will be sensed and $T_v$ will be calculated according to equations 1 and 3; then the processor will determine delta $T_{bf}$ according to equation 4. A read-out will be displayed on 82 for the use of the medical profession. Pressing switch 23 the third time removes the display and allows the unit to be ready for the next sequence of measurements.

Since U.S. Pat. No. 5,199,436 has shown in detail the required steps to program the microprocessor and the EEPROM, it is not necessary to repeat here either those steps or the additional ones indicated in the above paragraph.

Figure 3:
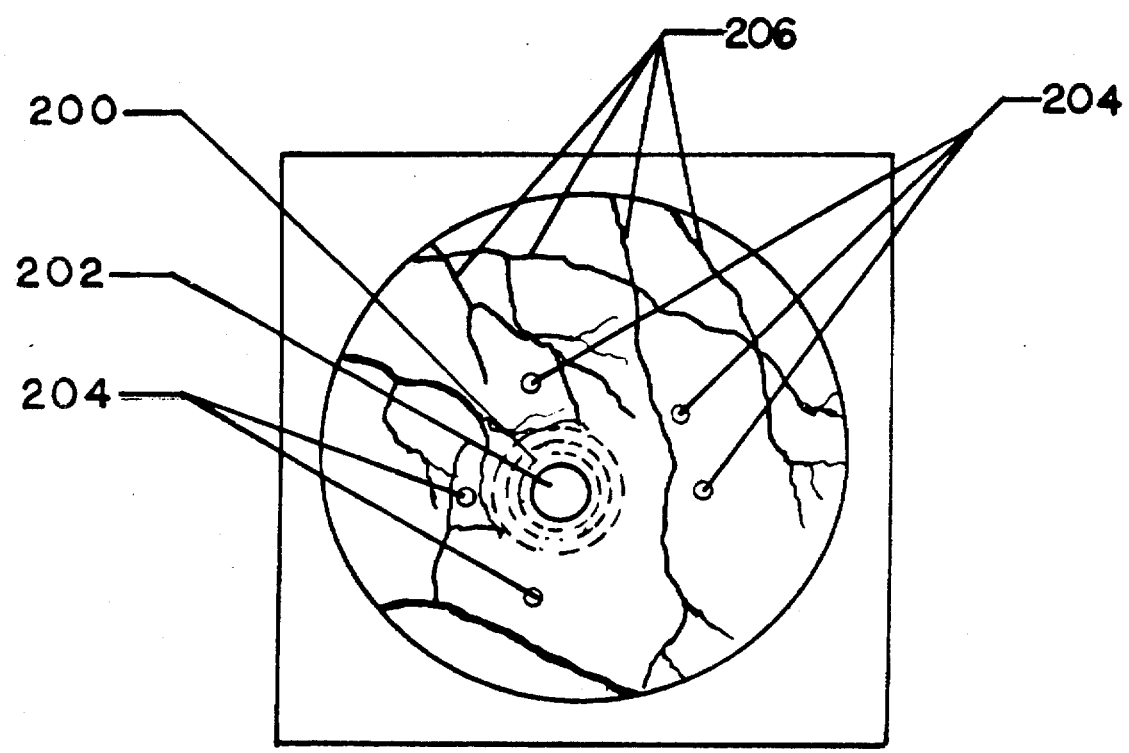
FIG. 3 is a simulated output signal map expressed as a drawing.

The aforementioned IR detector can be focused, either with or without the aid of the lens of the eye, on an emerging beam from the back of the eye where the choroid and internal blood vessels are located. Temperature within the eye can be referenced to the body core temperature via use of a tympanic measurement incorporated in the device. In this way accurate differential temperature readings encompassing a small area not previously available can be established to determine the lack of or increase in blood flow. The use of present day-state-of the art instrumentation to scan the eye and map the back of the, including the macula area, can be utilized. Computer technology can be employed to indicate those locatable spots scanned on a map and produce hard copies of the results, as indicated in the simulation shown in FIG. 3. Shown in FIG. 3 are: the macula 200, the central avascular fovea 202, locatable spots 204 and arteries 206.

In addition, the mapped areas will represent tissue temperature of small spots of choroidal tissue a distance removed from venous or arterial flows which is useful in indicating the presence of one or several of the five vascular retinopathy diseases, and retinal infection, retinal hemorrhaging, arteriosclerosis; and degeneration of: the macula choroid, or other tissue within the eye.

It is well known by ophthalmic researchers that if a pressure surge is applied to the eye by means of a vacuum cup, or other device, the intra-ocular pressure is momentarily disrupted and the eye will compensate for the increase in pressure such that in a relatively short time the pressure returns to its original level. The rate of recovery in each individual will differ, which may be an indication of the state of health of the subject's eyes. By accurately tracking this phenomenon as a function of time, it could prove to be a valuable diagnostic indicator. This can be accomplished by the proposed invention by measuring the change in temperature as a function of time to determine the recovery rate of a patient's eyes after an imposition of applied pressure. Also, by calibrating the temperature at the macula and fovea sites to pressure (see application Ser. No. 08/199,636, entitled "Noncontacting Portable Infrared Intra-ocular Pressure Sensor"), the potential susceptibility of the patient to impending glaucoma may be realized.

I claim:

1. A system to detect diseased tissue within the eye comprising:

a first temperature sensor adapted to obtain the core temperature of a patient;

a second temperature sensor detecting infrared radiation supported within said first temperature sensor and adapted to obtain a series of spot temperatures at spots encompassing choroidal tissue of the eye of said patient;

a focusing means focusing said detected infrared radiation at said second temperature sensor;

a referenced oriented tracking means directing said second temperature sensor to avoid veins and arteries of said patient to provide said series of spot temperatures at spots encompassing said choroidal tissue of the eye of said patient;

computing means comprising a microprocessor calculating a set of signals proportional to the difference between said core temperature and each of said spot temperatures; and output means providing an output map of the set signals.

2. The claim in 1 where the reference oriented tracking means is providing a map of veins and other fixed features within the eye providing for repeatability of measurement over time.

3. The claim in 2 where said map utilizes said avoided veins and arteries to provide referent markings in said maps of said eye to improve said map of the said temperature oriented proportional signal to include spot locations.

4. The claim in 1 where said first temperature sensor is a tympanic temperature measuring sensor.

5. A system to detect diseased tissue within the eye comprising:

a first temperature sensor adapted to obtain the core temperature of a patient;

a second temperature sensor detecting infrared radiation supported within said first temperature sensor and adapted to obtain a series of spot temperatures at spots encompassing the choroidal tissue of the eye of said patient;

a focusing means focusing said detected infrared radiation at said second temperature sensor;

a reference oriented tracking means directing said second temperature sensor to avoid veins and arteries of said patient to provide said series of spot temperatures at spots encompassing the choroidal tissue of the eye of said patient;

computing means comprising a microprocessor calculating a set of signals proportional to the difference between said core temperature and each of said spot temperatures;

output means providing an output map of the set of signals;

a pressure changing means adapted to be in contact with part of the eye of said patient to apply a pressure surge to the eye;

recording means recording the recovery of the eye to said pressure surge as a function of time and temperature at said spots encompassing the choroidal tissue of the eye.

6. A system to detect diseased tissue within the eye comprising:

a first temperature sensor adapted to obtain the core temperature of a patient;

a second temperature sensor detecting infrared radiation supported within said first temperature sensor and adapted to obtain a series of spot temperatures at spots encompassing choroidal tissue of the eye of said patient;

a focusing means focusing said detected infrared radiation at said second temperature sensor;

a referenced oriented tracking means directing said temperature sensor to avoid veins and arteries of said patient to provide said series of spot temperatures at spots encompassing said choroidal tissue of the eye of said patient;

computing means comprising a microprocessor calculating a set of signals proportional to the difference between said core temperature and each of said spot temperatures;

output means providing an output map of the set signals;

said output map of the temperature oriented proportional signal maps define the types and magnitude of tissue damage or disease within said eye;

referenced oriented tracking means is a computer oriented direction tracking system inputing angle, focal information, and referent locations into a visible or storable plot related to said output map of the temperature oriented proportional signal.

7. A method to detect diseased tissue within the eye of a patient comprising:

obtaining the core temperature of said patient with a first temperature sensor;

detecting infrared radiation with a second temperature sensor supported within said first temperature sensor and obtaining a series of spot temperatures at spots encompassing choroidal tissue of said eye of said patient;

focusing said detected infrared radiation at said second temperature sensor with a focusing means;

directing said temperature sensor to avoid veins and arteries of said patient to provide said series of spot temperatures at spots encompassing said choroidal tissue of said eye of said patient by using a reference oriented tracking means;

using the signed difference between the first temperature sensor means output and said second temperature sensor means output indicating susceptibility to the five vascular retinopathies diseases of said tissues within said eye of said patient.

8. The method in 7 using said signed difference between said first sensing output and said second sensing output to indicate susceptibility to the five vascular retinopathies diseases, retinal infection, retinal hemorrhaging, arteriosclerosis; and degeneration of the tissues within said eye of said patient.

9. A method to detect the diseased tissue within the eye of a patient comprising:

obtaining the core temperature of said patient with a first temperature sensor;

detecting infrared radiation with a second temperature sensor supported within said first temperature sensor and obtaining a series of spot temperatures at spots encompassing choroidal tissue of said eye of said patient;

focusing said detected infrared radiation at said second temperature sensor with a focusing means;

directing said temperature sensor to avoid veins and arteries of said patient to provide said series of spot temperatures at spots encompassing said choroidal tissue of said eye of said patient by using a reference oriented tracking means;

using the signed difference between the first temperature sensor means output and said second temperature sensor means output indicating susceptibility to the five vascular retinopathies diseases of said tissues within said eye of said patient;

applying a pressure surge by contacting with said eye by pressure changing means;

recording graphically or electronically as a function of time at said locatable spots the temperature recovery of said eye to said pressure surge;

wherein said temperature recovery uses the signed differences between the first said temperature sensing output and the second said temperature sensing output to indicate the presence of the five vascular retinopathies, the retinal infection, retinal hemorrhaging, arteriosclerosis, and degeneration of tissues within said eye.

10. A method to detect the diseased tissue within the eye of a patient comprising:

obtaining the core temperature of said patient with a first temperature sensor;

detecting infrared radiation with a second temperature sensor supported within said first temperature sensor and obtaining a series of spot temperatures at spots encompassing choroidal tissue of said eye of said patient;

focusing said detected infrared radiation at said second temperature sensor with a focusing means;

directing said temperature sensor to avoid veins and arteries of said patient to provide said series of spot temperatures at spots encompassing said choroidal tissue of said eye of said patient by using a reference oriented tracking means;

using the signed difference between the first temperature sensor means output and said second temperature sensor means output indicating susceptibility to the five vascular retinopathies diseases of said tissues within said eye of said patient;

applying a pressure surge by contacting with said eye by pressure changing means;

recording graphically or electronically as a function of time at said locatable spots the temperature recovery of said eye to said pressure surge;

and providing the signed differences between the first said temperature sensing output and the second said temperature sensing output by using the temperature recovery as detected by said second temperature sensor to indicate impending glaucoma within said eye.

* * * * *